(12) United States Patent
Chojin (10) Patent No.: US 8,764,748 B2
(45) Date of Patent: Jul. 1, 2014

(54) END EFFECTOR ASSEMBLY FOR ELECTROSURGICAL DEVICE AND METHOD FOR MAKING THE SAME

(75) Inventor: Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 900 days.

(21) Appl. No.: 12/361,375

(22) Filed: Jan. 28, 2009

(65) Prior Publication Data
US 2009/0198233 A1 Aug. 6, 2009

Related U.S. Application Data

(60) Provisional application No. 61/026,499, filed on Feb. 6, 2008.

(51) Int. Cl.
*A61B 18/14* (2006.01)

(52) U.S. Cl.
USPC .............. 606/51; 606/50; 606/48; 606/52

(58) Field of Classification Search
USPC ...................................... 606/42–51
See application file for complete search history.

(56) References Cited

U.S. PATENT DOCUMENTS

| | | | |
|---|---|---|---|
| 371,664 A | 10/1887 | Brannan, et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 1,822,330 A | 9/1931 | Ainslie | |
| 1,852,542 A | 4/1932 | Sovatkin | |
| 2,002,594 A | 5/1935 | Wappler et al. | |
| 2,011,169 A | 8/1935 | Wappler | |
| 2,031,138 A * | 2/1936 | Hall .............................. | 228/145 |
| 2,031,682 A | 2/1936 | Wappler et al. | |
| 2,054,149 A | 9/1936 | Wappler | |
| 2,176,479 A | 10/1939 | Willis | |
| 2,305,156 A | 4/1941 | Grubel | |
| 2,279,753 A | 4/1942 | Knopp | |
| 2,327,353 A | 8/1943 | Karle | |
| 2,632,661 A | 8/1948 | Cristofv | |
| 2,668,538 A | 2/1954 | Baker | |
| 2,796,065 A | 6/1957 | Kapp | |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

(Continued)

*Primary Examiner* — Laura Bouchelle (57) ABSTRACT

An end effector assembly for use with a forceps is provided. The end effector assembly including a pair of opposing jaw members operatively connected to each other about a pivot. Each jaw member includes a structural support member having a seal plate secured thereto. Each of the seal plates defines a slot having a depth and configured to translate a knife blade therethrough. The combined depth of the slot is greater than the height of the knife blade.

8 Claims, 6 Drawing Sheets

(56) References Cited

U.S. PATENT DOCUMENTS

| | | |
|---|---|---|
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |

(56) References Cited

U.S. PATENT DOCUMENTS

| | | |
|---|---|---|
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,512,721 A | 4/1996 | Young et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |

(56) References Cited

U.S. PATENT DOCUMENTS

| | | |
|---|---|---|
| 5,814,043 A | 9/1998 | Shapeton |
| 5,814,054 A | 9/1998 | Kortenbach et al. |
| 5,817,083 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |

(56) References Cited

U.S. PATENT DOCUMENTS

| | | |
|---|---|---|
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |

(56) References Cited

U.S. PATENT DOCUMENTS

| | | |
|---|---|---|
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0052778 A1 | 3/2006 | Chapman et al. |
| 2006/0052779 A1 | 3/2006 | Hammill |
| 2006/0064085 A1* | 3/2006 | Schechter et al. ............... 606/50 |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |

(56) References Cited

U.S. PATENT DOCUMENTS

| | | |
|---|---|---|
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1* | 5/2007 | Dumbauld et al. ............ 606/51 |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

FOREIGN PATENT DOCUMENTS

| | | |
|---|---|---|
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 | 4/1990 |
| EP | 0467501 | 1/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0986990 | 3/2000 |
| EP | 1034747 | 9/2000 |
| EP | 1034748 | 9/2000 |
| EP | 1025807 | 10/2000 |
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1535581 | 6/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1707143 | 10/2006 |
| EP | 1769765 | 4/2007 |

(56) References Cited

FOREIGN PATENT DOCUMENTS

| | | |
|---|---|---|
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback—controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.

(56) References Cited

OTHER PUBLICATIONS

Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct 1965 pp. 823-831.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.

* cited by examiner

END EFFECTOR ASSEMBLY FOR ELECTROSURGICAL DEVICE AND METHOD FOR MAKING THE SAME

CROSS-REFERENCE TO RELATED APPLICATIONS

This application claims the benefit of priority to U.S. Provisional Application Ser. No. 61/026,499 entitled "END EFFECTOR ASSEMBLY FOR ELECTROSURGICAL DEVICE AND METHOD FOR MAKING THE SAME" filed Feb. 6, 2008 by Edward Chojin, which is incorporated by reference herein.

BACKGROUND

1. Technical Field

The present disclosure relates to an electrosurgical forceps and more particularly, the present disclosure relates to electrosurgical forceps, which employ an end effector assembly configured for receiving a knife blade, or portion thereof, within a seal plate.

2. Description of Related Art

As is known in the art, bipolar forceps typically employ end effector assemblies that include one or more jaw members. Generally, the jaw members include a structural support member, an insulative member, and a thin seal plate. The structural support member and the thin seal each may include a slot adapted to receive a knife blade, or portion thereof.

The structural support and the thin seal plate of the jaw members may be over-molded and/or stamped together, wherein the slot of the seal plate is configured to align with a slot or groove on the structural support member such that when the jaw members are in a closed configuration, the knife blade can move longitudinally therein. Because the knife blade, the slot in the structural support member, and slot in the seal plate need to be in almost perfect alignment with each other, machining tolerances during the manufacture process must be kept at a minimum. Thus, manufacturing conventional end-effector assemblies is generally time-consuming and requires a multi-step process, which, in turn, may lead to increased cost to the manufacturer.

SUMMARY OF THE DISCLOSURE

An end effector assembly for use with a forceps is provided. The end effector assembly including a pair of opposing jaw members operatively connected to each other about a pivot. Each jaw member includes a structural support member having a seal plate secured thereto. In an embodiment, each of the structural supports includes one or more apertures extending therein configured to facilitate structural engagement of the structural support member to a respective seal plate. In embodiments, the aperture may extend through the entire thickness of the seal plate. Alternatively, the aperture does not extend through the entire thickness of the seal plate. Each of the seal plates defines a slot having a depth and configured to translate a knife blade therethrough. The combined depth of the slot is greater than the height of the knife blade.

In an embodiment, the seal plates are secured to their respective structural support members via at least one of welding, soldering and brazing. The type of weld may be selected from the group consisting of resistance welding, ultrasonic welding, gas welding, energy beam welding, explosion welding, and solid state welding.

A method for manufacturing an end effector assembly for use with a bipolar forceps is provided. The method including the steps of: a) providing a structural support, the structural support including at least one aperture associated with a top surface thereof; b) providing a seal plate, the seal plate defining a slot configured to translate a knife blade therethrough; and c) utilizing the at least one aperture to gain access to couple the seal plates to the structural support.

DETAILED DESCRIPTION

Detailed embodiments of the present disclosure are disclosed herein; however the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As mentioned above, conventional electrosurgical forceps include end-effector assemblies that include a pair of opposing jaw members each having an insulating structural support member and a thin seal plate, which may include a knife blade slot adapted to receive a knife blade or portion thereof. Typically, the structural support member and the thin seal plate of the jaw members are stamped or over-molded together.

Structural integrity of the jaw members is provided by their respective structural support members. The insulative support electrically isolates tissue from the thin seal plate and, in some instances, may also be configured to provide additional structural integrity the jaw member. Because the overall structural integrity of the jaw members is provided by their respective structural support members, the seal plates typically are manufactured relatively thin and provide minimal, if any, structural integrity to each respective jaw member.

Conventional seal plates include an electrically conductive tissue contacting surface configured to cause an effect to tissue, e.g., a tissue seal. As mentioned above, in some instances the seal plate may include a slot defined there along configured to receive a knife blade, or portion thereof.

Normally, the slot of the seal plate will be configured to align with a groove or slot located on the structural support member in such a manner that the knife blade, or portion thereof, may translate therein. For the reasons stated above, having end effector assemblies including a structural support member and a seal plate configured in such a manner may prove to be time-consuming and costly to manufacture.

The present disclosure provides an end-effector assembly that includes opposing jaw members each of which includes a structural support member and a seal plate that includes a slot, wherein the seal plates are configured in such a manner that the knife blade, or portion thereof, may translate within the slots of the seal plates independently from their respective structural support members. That is, the seal plates may each have a thickness that allows the knife blade to translate within the slots of the seal plates without extending into their respective structural support members.

Additionally, because of the thickness of the seal plates, the structural support members and their respective seal plates may each be secured to one another via a weld or the like and alignment issues are obviated.

Figure 1:
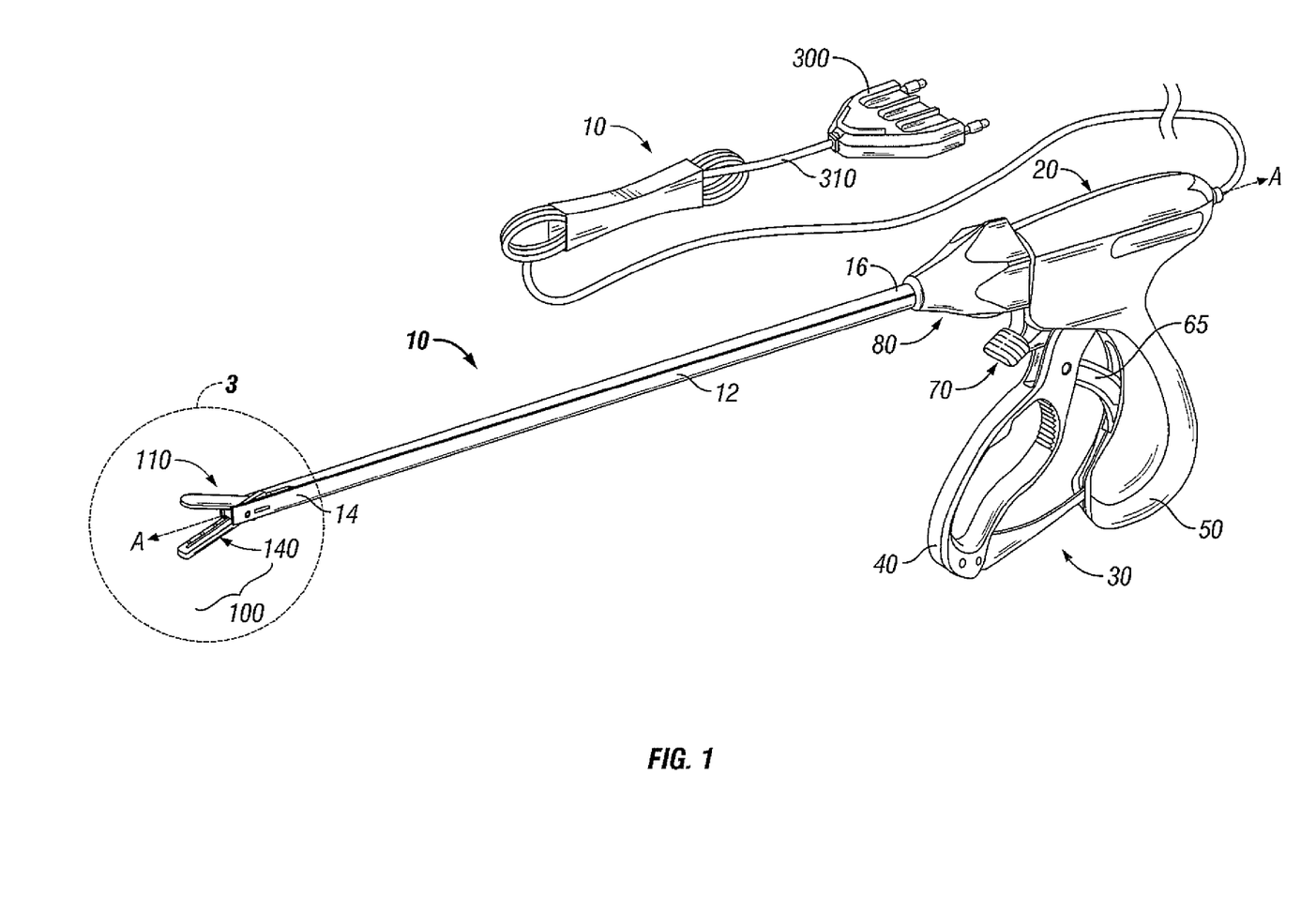
FIG. 1 is a perspective view of a bipolar forceps in accordance with an embodiment of the present disclosure.
Figure 2:
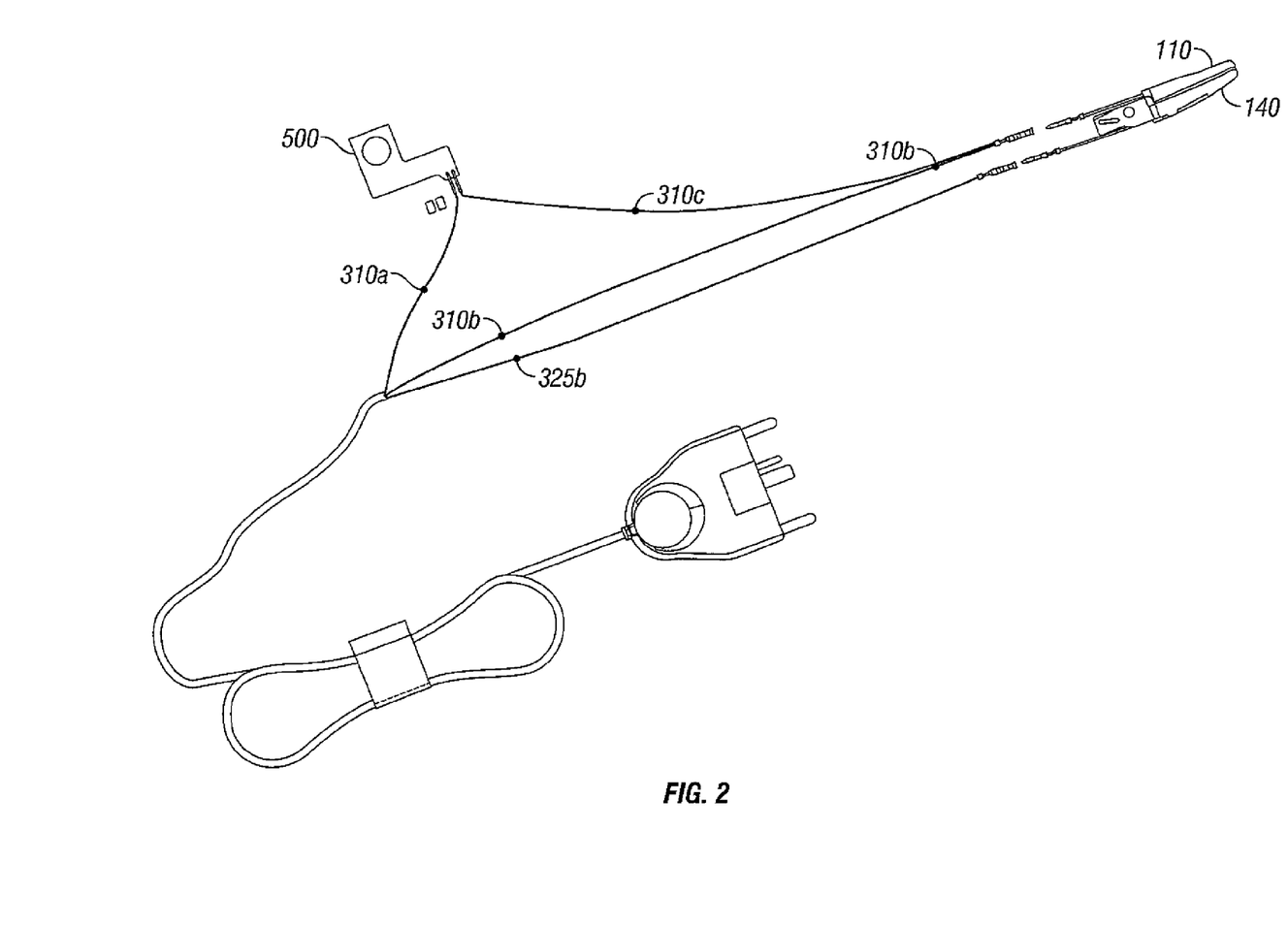
FIG. 2 illustrates an electrical wring diagram for the bipolar forceps depicted in FIG. 1 in accordance with the present disclosure.

Turning now to FIG. 1, one embodiment of an electrosurgical forceps 10 is shown. For the remainder of the disclosure it will be assumed that the electrosurgical forceps is a bipolar forceps; keeping in mind that any suitable electrosurgical forceps may be employed with the present disclosure. Bipolar forceps 10 is shown for use with various electrosurgical procedures and generally includes a housing 20, a handle assembly 30, a rotating assembly 80, a trigger assembly 70, a drive assembly 130 (not shown), and an end effector assembly 100, which may be operatively connected to the drive assembly 130. End effector assembly 100 includes opposing jaw members 110 and 140, which mutually cooperate to grasp, seal and, in some cases, divide large tubular vessels and large vascular tissues. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument; however, it is contemplated that an open version of the forceps may also include the same or similar operating components and features as described below.

Forceps 10 includes a shaft 12, which has a distal end 14 dimensioned in such a manner that a drive rod 132 of drive assembly 130 mechanically engages the end effector assembly 100 and a proximal end 16 mechanically engages the housing 20. In the drawings and in the descriptions that follow, the term "proximal," as is traditional, will refer to the end of the forceps 10 that is closer to the user, while the term "distal" will refer to the end that is farther from the user.

Handle assembly 30 includes a fixed handle 50 and a movable handle 40. Fixed handle 50 is integrally associated with housing 20 and handle 40 is movable relative to fixed handle 50. Fixed handle 50 may include one or more ergonomic enhancing elements to facilitate handling, e.g., scallops, protuberances, elastomeric material, etc.

Movable handle 40 of handle assembly 30 is ultimately connected to drive assembly 130 including drive rod 132, which together mechanically cooperate to impart movement of jaw members 110 and 140 to move from an open position, wherein the jaw members 110 and 140 are disposed in spaced relation relative to one another, to a clamping or closed position, wherein the jaw members 110 and 140 cooperate to grasp tissue therebetween.

Rotating assembly 80 is operatively associated with the housing 20 and is rotatable approximately 180 degrees about a longitudinal axis "A-A" defined through shaft 12 (see FIG. 1).

Forceps 10 also includes an electrosurgical cable 310 that connects the forceps 10 to a source of electrosurgical energy, e.g., a generator 500 (shown schematically). It is contemplated that generators such as those sold by Valleylab—a division of Tyco Healthcare LP, located in Boulder Colo. may be used as a source of electrosurgical energy, e.g., Ligasure™ Generator, FORCE EZ™ Electrosurgical Generator, FORCE FX™ Electrosurgical Generator, FORCE 1C™, FORCE 2™ Generator, SurgiStat™ II or other suitable generators which may perform different or enhanced functions.

For a more detailed description of handle assembly 30, movable handle 40, rotating assembly 80, electrosurgical cable 310 (including line-feed configurations and/or connections), and drive assembly 130 reference is made to commonly owned patent application Ser. No. 10/369,894, filed on Feb. 20, 2003, entitled VESSEL SEALER AND DIVIDER AND METHOD OF MANUFACTURING THE SAME.

End effector assembly 100 includes opposing jaw members 110 and 140. Jaw members 110 and 140 are generally symmetrical and include similar component features that cooperate to effect the sealing and/or dividing of tissue. As a result and unless otherwise noted, only jaw member 110 and the operative features associated therewith are described in detail herein but as can be appreciated, many of these features apply to jaw member 140 as well.

Figure 3A:
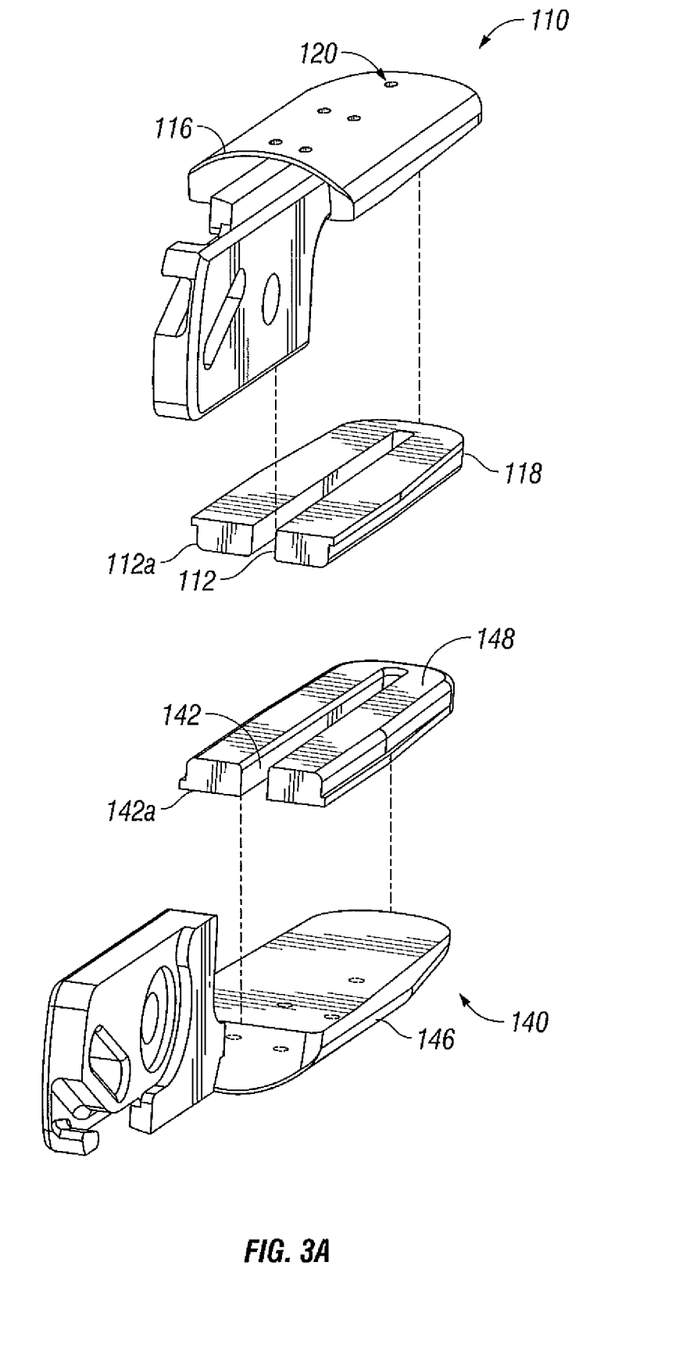
FIG. 3A is an exploded view of the area defined by reference numeral 3 in FIG. 1 illustrating a structural support member and a seal plate in accordance with an embodiment of the present disclosure.
Figure 3B:
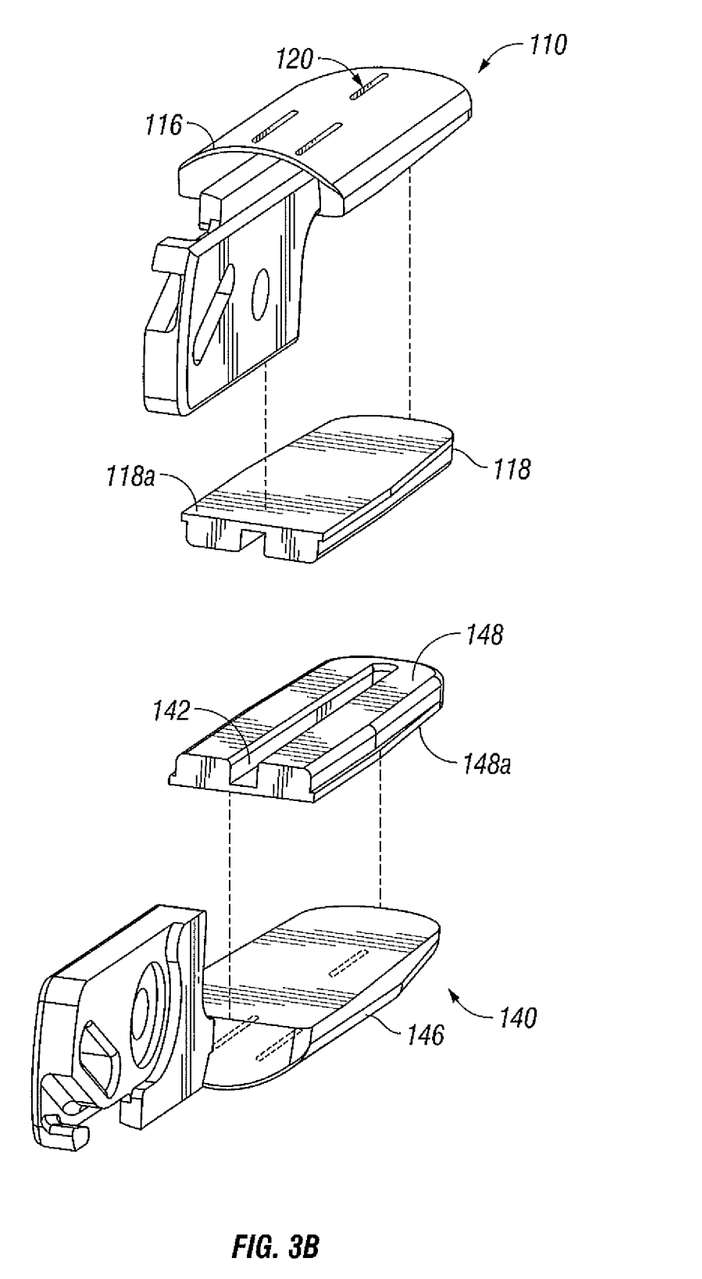
FIG. 3B is an exploded view of the area defined by reference numeral 3 in FIG. 1 illustrating a structural support member and a seal plate in accordance with an alternate embodiment of the present disclosure.

Turning now to FIGS. 3A and 3B, jaw member 110 is shown. Jaw member 110 includes a structural support member 116 and an electrically conductive seal plate 118 (hereinafter seal plate 118) defining a slot 112 therein. The structural support 116 is dimensioned to mechanically engage, as explained in more detail below, the seal plate 118. Similarly, jaw member 140 includes a structural support member 146 and an electrically conducive seal plate 148 defining a slot 142 therein.

Figure 4A:
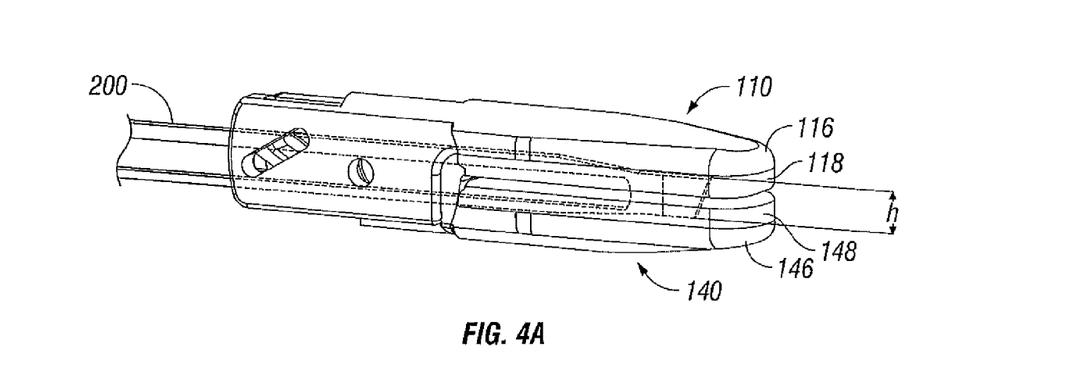
FIGS. 4A and 4B are side and cross sectional views, respectively, illustrating a knife blade within the seal plate depicted in FIG. 3B.
Figure 4B:
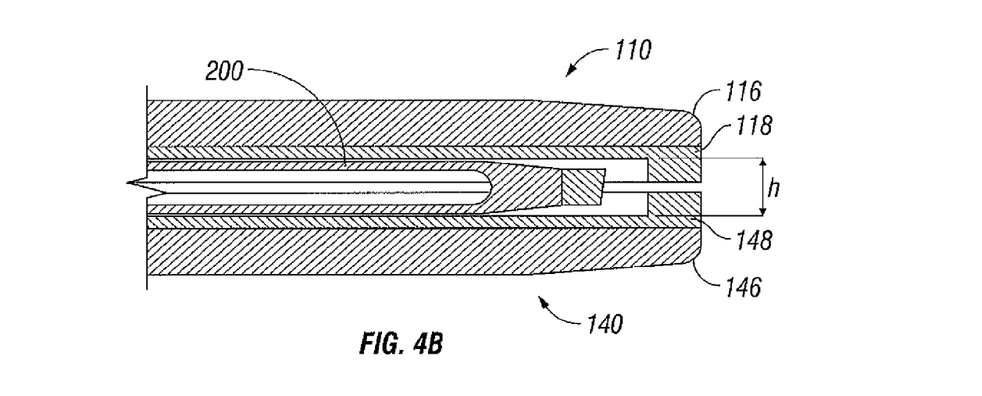

With reference to FIGS. 4A and 4B, seal plates 118 and 148 are configured in such a manner that when jaw members 110 and 140 are in a closed configuration, a knife blade 200, or portion thereof, translates within slot 112 of seal plate 118 and slot 142 of seal plate 148 independent of structural members 116 and 148, respectively. That is, seal plates 118 and 148, or portions thereof have a combined thickness, when in a closed configuration, that is greater than a height "h" of knife blade 200. For example, each of seal plates 118 and 148 of jaw member 110 and 140, respectively, may each have a thickness that is at least greater than one-half the height "h" of knife blade 200. As a result, knife blade 200 is incapable of or prevented from extending into structural members 116 and 146 and alignment and tolerance issues are altogether avoided during manufacture.

In other words, 118 and 148 of jaw members 110 and 140, respectively, have thicknesses that may not necessarily be equal to one another, but ultimately equal to the height "h" of knife blade 200 when the jaw members are in a closed configuration.

Seal plates 118 and 148 may also have a thickness that varies (i.e., non-uniform) from a proximal end to a distal end, or intermediate therebetween, of each of the seal plates. For example, seal plates 118 and 148 each may have a proximal end that has a thickness that is slightly larger than a thickness at a distal end thereof depending on a particular purpose.

Seal plates 118 and 148 each include a top surface 118*a* and 148*a*, respectively, which are herein defined as the surface that secures to the structural support member and a bottom surface, which are herein defined as surface that contacts tissue. Slots 112 and 142 extend distally from a proximal end 112*a* and 142*a* of their respective seal plates 118, 148 and provide a path for longitudinal translation of the knife blade 200 therein. Slots 112 and 142 may be opened at the top surface of their respective seal plates (FIG. 3A). Alternatively, slots 118 and 148 may be closed at the top surface of their respective seal plates (FIG. 3B).

Seal plates 118 and 148 defining knife blade slots 112 and 142, respectively, are configured to join to their respective structural members via one or more known manufacturing techniques, e.g., ultrasonic welding, heat welding, arc welding, and so on. Welding techniques suitable for joining structural member 116 to seal plate 118 include but are not limited to resistance welding, gas welding, energy beam welding, explosion welding, and solid state welding.

With reference to FIGS. 3A and 3B, structural support member 116 is shown and is manufactured from any suitable material known in the art including but not limited to metal, plastic and the like. Structure support member 116 is configured to couple to seal plate 118, such that jaw members 110 and 140 are moveable from an open configuration to a closed configuration wherein they may cooperate to effect the sealing and/or dividing of tissue.

Figure 5A:
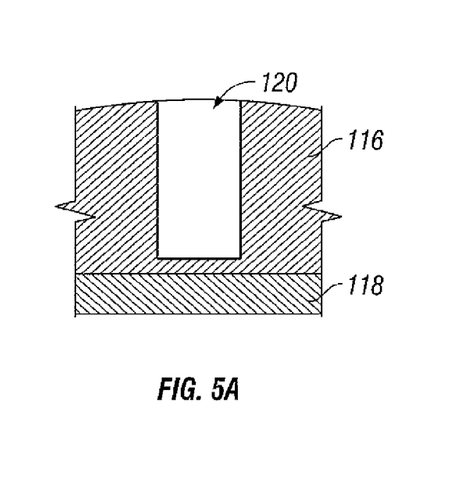
FIGS. 5A and 5B illustrate the structural support member and the seal plate before and after a weld joint is formed.
Figure 5B:
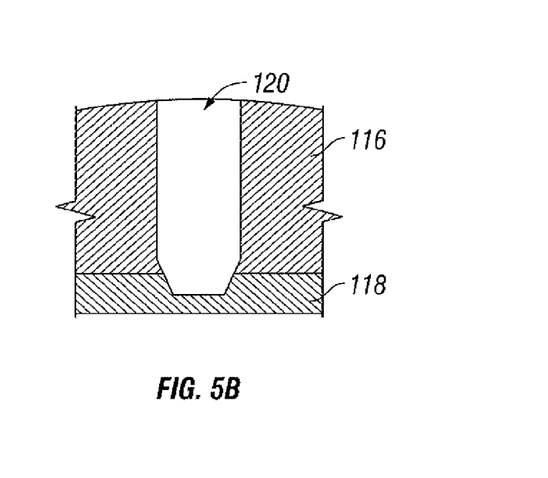

Located on structural support members 116 and 140, or portions thereof, are one or more bored apertures 120 (FIGS. 3A and 3B). Apertures 120 may have any suitable shape, such as holes, slots, grooves, and so on, which are configured to extend within structural support 116 and are dimensioned for joining seal plate 118, or portion thereof, to structural support member 116, as shown in FIG. 5A or 5B. For example, aperture 120 may be configured such that structural support member 116 and seal plate 118 may be joined together via a weld formed therebetween. With this purpose in mind, aperture 120 does not fully extend to seal plate 118 (FIG. 5A). As a result, a portion of structural support 116 is kept between aperture 120 and the top surface 118a of seal plate 118. The portion kept between structural support 116 and seal plate 118 forms part of the weld (FIG. 5B).

Structural members 116 and 146 may be joined to their respective seal plates 118, 148 via one or more of the above welding techniques or by other fastening methods known in the art, e.g., soldering or brazing.

In use, prior to sealing tissue, jaw members 110 and 140 may be initially in an open configuration, each disposed at an angle θ relative to the longitudinal axis "X. When tissue is ready to be grasped for sealing, a user positions tissue between jaw members 110 and 140, and squeezes handle 40 which, in turn, causes jaw members 110 and 140 to move from the open configuration to a closed configuration. After tissue is grasped between jaw members 110 and 140, electrosurgical energy may be transmitted to the jaw members 110 and 140 effecting a tissue seal therebetween (e.g., coagulation).

If tissue is to be cut, while tissue is grasped between jaw members 110 and 140, a user activates knife blade 200 such that knife blade 200 extends longitudinally through slots 112 and 142 of seal plates 118 and 148, respectively, effecting a tissue cut therebetween.

Upon completion of treating target tissue (e.g., sealing and/or cutting), a user releases handle 40, which, in turn, causes jaw members 110 and 140 to return to their initial open configuration, wherein they will again be disposed at an angle θ relative to the longitudinal axis "X".

Figure 6:
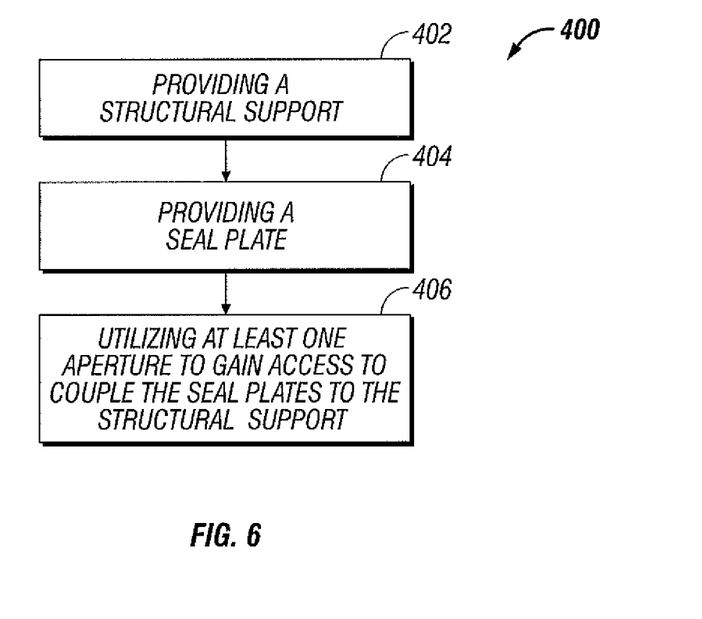
FIG. 6 is a flowchart illustrating a method for manufacturing an end effector assembly.

With reference to FIG. 6, a method 400 for manufacturing an end effector assembly for use with a bipolar forceps is shown. At step 402, a structural support including at least one aperture associated with a top surface thereof is provided. At step 404, a seal plate defining a slot configured to translate a knife blade therethrough is provided. And at step 406, one or more apertures configured to gain access to couple the seal plates to the structural support is utilized.

From the foregoing and with reference to the various figure drawings, those skilled in the art will appreciate that certain modifications can also be made to the present disclosure without departing from the scope of the same.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for use with a forceps, comprising;
   a pair of opposing jaw members operatively connected to each other about a pivot, each jaw member including a structural support member having a seal plate secured thereto, each of the seal plates having electrically conductive top and bottom surfaces with a slot defined therebetween having a depth and configured to translate a knife blade therethrough, wherein the top surfaces are utilized to secure the seal plates to the respective structural support member, the slots extending only partially through a full thickness of the seal plates, the combined depth of the slots being greater than a height of the knife blade such that during translation of the knife blade through the slots, the knife blade does not extend into the structural support members,
   wherein each of the structural support members includes at least one aperture extending partially therethrough such that at least a portion of each structural support member remains between the aperture and the respective seal plate to facilitate coupling of the structural support members to the respective seal plates.

2. The end effector assembly according to claim 1, wherein the seal plates are secured to their respective structural support members via at least one of welding, soldering or brazing.

3. The end effector assembly according to claim 2, wherein the type of welding is selected from the group consisting of resistance welding, ultrasonic welding, gas welding, energy beam welding, explosion welding, and solid state welding.

4. The end effector assembly according to claim 1, wherein the seal plates vary in thickness.

5. A method for manufacturing a jaw member of an end effector assembly for use with as forceps, the method comprising:
   providing as structural support member, the structural support member including at least one aperture associated with a top surface thereof and extending partially therethrough;
   providing a seal plate, the seal plate having electrically conductive top and bottom surfaces having a slot defined therebetween, wherein the top surface is utilized to secure the seal plate to the structural support member, the slot extending only partially through a full thickness of the seal plate, the seal plate configured to translate a knife blade therethrough such that during translation of the knife blade through the slot, the knife blade does not extend into the structural support member; and
   utilizing the at least one aperture to couple the seal plate to the structural support member.

6. The method of according to claim 5, wherein utilizing the at least one aperture to couple the seal plate to the structural support member comprises coupling the seal plate to the structural support member by a process selected from the group consisting of welding, soldering and brazing.

7. The method according to claim 6, wherein utilizing the at least one aperture to the seal plate to the structural support member comprises coupling the seal plate to the structural support member by the process selected from the group consisting of resistance welding, ultrasonic welding, gas welding, energy beam welding, explosion welding, and solid state welding.

8. An end effector assembly for use with a forceps, comprising:
   a pair of opposing jaw members operatively connected to each other about a pivot, each jaw member including a structural support member having a seal plate secured thereto, each of the seal plates having electrically conductive top and bottom surfaces with a slot defined therebetween having a depth and configured to translate a knife blade therethrough, wherein the top surfaces are utilized to secure the seal plates to the respective structural support member, the slots extending only partially through a full thickness of the seal plates, the combined depth of the slots being greater than a height of the knife blade such that during translation of the knife blade through the slots, the knife blade does not extend into the structural support members;
   wherein each of the structural support members includes at least one aperture extending partially therethrough such that at least a portion of each structural support member remains between the at least one aperture and the seal plate and is configured to form part of a weld therebetween to facilitate structural engagement of the structural support member to a respective seal plate.

* * * * *